United States Patent
Brandt et al.

(10) Patent No.: US 10,152,832 B1
(45) Date of Patent: *Dec. 11, 2018

(54) SYSTEMS AND METHOD FOR LIVE AND REPLAY UTILIZATION AND TRACKING OF VEHICULAR MOVEMENT AND RESPONSE

(71) Applicant: Pulse Live, LLC, Tyler, TX (US)

(72) Inventors: Joshua Brandt, San Antonio, TX (US); Randal Matthew, Tyler, TX (US)

(73) Assignee: GenCore Candeo Ltd., Tyler, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/198,186

(22) Filed: Jun. 30, 2016

Related U.S. Application Data

(63) Continuation of application No. 14/013,984, filed on Aug. 29, 2013, now Pat. No. 9,646,498.

(60) Provisional application No. 61/720,814, filed on Oct. 31, 2012.

(51) Int. Cl.
  *G07C 5/06* (2006.01)
  *G07C 5/00* (2006.01)

(52) U.S. Cl.
  CPC ............ *G07C 5/06* (2013.01); *G07C 5/008* (2013.01)

(58) Field of Classification Search
  CPC ............ G01C 21/36; G01C 21/3647; G06Q 30/0251; G06Q 30/0266; B60K 2350/1072; B60K 37/02; B60L 13/04; B60L 2200/26; B60R 16/0232; B60R 16/037; G08G 1/095; G08G 1/096716; G08G 1/096741; G08G 1/09675; G08G 1/096775; G08G 1/096844; G08G 1/096872; H04W 12/06; H04W 4/046; B61B 13/08
  See application file for complete search history.

(56) References Cited

U.S. PATENT DOCUMENTS

| 5,223,844 A | * | 6/1993 | Mansell | ............... B60R 25/04 340/426.19 |
| 5,636,122 A | * | 6/1997 | Shah | .................... G01C 21/36 340/990 |
| 5,758,313 A | * | 5/1998 | Shah | ................. G01C 21/3446 340/990 |

(Continued)

OTHER PUBLICATIONS

Brandt et al., "Systems and Methods for Live and Replay Utilization and Tracking of Vehicular Movement and Response," U.S. Appl. No. 14/013,984, filed Aug. 29, 2013, 36 pages.

(Continued)

*Primary Examiner* — Fekadeselassie Girma
(74) *Attorney, Agent, or Firm* — Perkins Coie LLP

(57) ABSTRACT

Systems and methods for live utilization and tracking of vehicular movement producing a fluid representation of the movement of vehicles and means to evaluate vehicle movement/activities relative to response requirements may be provided. Accordingly, real-time evaluations and/or corrections may be made based on this improved tracking of movement/activities. Replay analysis of movement/activities that have already occurred may be provided to evaluate and make adjustments for future responses and activities. Colors and other unique display items may be used to highlight different activities, movements and/or timing for completion within an online mapping application. Layering of different mapping displays also may be provided.

25 Claims, 6 Drawing Sheets

(56) References Cited

U.S. PATENT DOCUMENTS

| | | | | |
|---|---|---|---|---|
| 6,415,219 | B1* | 7/2002 | Degodyuk | G08G 1/20 |
| | | | | 340/531 |
| 9,224,293 | B2* | 12/2015 | Taylor | G08G 1/08 |
| 2003/0080933 | A1 | 5/2003 | Kondoh | |
| 2004/0057570 | A1 | 3/2004 | Power et al. | |
| 2004/0164963 | A1* | 8/2004 | Ono | G06F 3/016 |
| | | | | 345/167 |
| 2006/0164259 | A1* | 7/2006 | Winkler | G08G 1/127 |
| | | | | 340/944 |
| 2008/0231446 | A1* | 9/2008 | Cresto | G06Q 10/08 |
| | | | | 340/572.1 |
| 2010/0160013 | A1* | 6/2010 | Sanders | G01S 5/0027 |
| | | | | 463/6 |
| 2010/0250111 | A1* | 9/2010 | Gutierrez | G01C 21/3697 |
| | | | | 701/532 |
| 2011/0181443 | A1* | 7/2011 | Gutierrez | G01C 21/3691 |
| | | | | 340/990 |
| 2011/0320492 | A1* | 12/2011 | Inghelbrecht | G06Q 40/08 |
| | | | | 707/776 |
| 2013/0179027 | A1* | 7/2013 | Mitchell | G06Q 10/063 |
| | | | | 701/29.3 |
| 2015/0042573 | A1* | 2/2015 | Grant | G06F 3/016 |
| | | | | 345/173 |

OTHER PUBLICATIONS

Brandt et al., "Systems and Methods for Live and Replay Utilization and Tracking of Vehicular Movement and Response," U.S. Appl. No. 61/720,814, filed Oct. 31, 2012, 36 pages.

* cited by examiner

30

M2140 - OS

| | |
|---|---|
| Crew: | Mike Roesbury |
| | John Niven |
| Shift Remaining: | 09:25:00 |
| Velocity: | 0 |
| Primary EID: | 434086 |
| Secondary EID: | 434086 |
| Incident: | 12000020707 |
| Destination: | 2316 96TH AV OA.7 |
| Nature: | BREATHING PROBLEMS DIFFICULTY SPEAKING BETWEEN BREATHS |
| Scene: | 2316 96TH AV |
| | Oakland |
| Directions: | To here - From here |

*FIG. 3*

SYSTEMS AND METHOD FOR LIVE AND REPLAY UTILIZATION AND TRACKING OF VEHICULAR MOVEMENT AND RESPONSE

CROSS REFERENCE TO RELATED APPLICATIONS

This application is a continuation of U.S. patent application Ser. No. 14/013,984, filed on Aug. 29, 2013, which itself is a non-provisional patent application of U.S. Patent Application Ser. No. 61/720,814 filed Oct. 31, 2012, each of which is hereby incorporated by reference for all purposes.

FIELD OF THE DISCLOSURE

The present disclosure generally relates to vehicle tracking, and more particularly to live and replay utilization and tracking of vehicular movement and response.

BACKGROUND

A dispatched emergency vehicle needs to respond to a call and reach the scene as quickly as possible. Use of GPS tracking may assist the emergency vehicle and/or dispatcher in determining the quickest route to the scene; however, the emergency vehicle does not always have the benefit of receiving real-time data about the call or route and/or the ability to interact directly with the dispatcher in a visual form. Other than by communicating through cellular or paging technology, the dispatcher also may be limited in the amount of information that he/she receives related to the dispatched emergency vehicle and accordingly may have limited ability to provide updates in real-time to ensure that the emergency vehicle reaches the scene in the specified amount of time. Further, the dispatcher or operator may be limited in the ability to review what happened when an emergency vehicle responded to a call other than reviewing time stamps from an onboard tracking device associated with an emergency vehicle.

SUMMARY

Embodiments of the present disclosure may provide a system for live and replay tracking of vehicular movement, the system comprising a live module that may evaluate and make corrections to the vehicular movement in real-time, and a replay module that may replay the vehicular movement and evaluate historical data concerning the vehicular movement. The live module and the replay module each may utilize a menu and a mapping application. The live module and replay module may share data about the vehicular movement stored in one or more databases and transmitted via one or more servers over a communication network. The system may further comprise a reporting module to evaluate the vehicular movement, wherein reports may be generated based on the data about the vehicular movement stored in the one or more databases, the reports using one or more parameters including date, type of call and timeliness of response to call. The menu of the live module and the replay module may selectively display at least one of the following items within the respective mapping application: a post location, a call location, an allowable response time remaining to reach a call location, a reporting zone, a current unit status, and satellite imagery associated with a post or call location.

Other embodiments of the present disclosure may provide a system for live tracking and evaluation of an emergency unit responding to a call, the system comprising a module including a menu providing one or more selectable items and a mapping application, wherein the one or more selectable items may be selectively displayed within the mapping application as the emergency unit responds to the call, and a communication link to receive and transmit information related to the emergency unit responding to the call. The one or more selectable items may comprise reporting zones, active responses, units, places, and posts. The mapping application may display a colored line connecting the emergency unit to a response location, wherein the color of the colored line may correspond to the priority level of the call associated with the response location. The active responses may provide information about the determinant, time remaining before a response is considered late, and an identification of the emergency unit assigned to respond to the call. The mapping application may selectively display information about more than one emergency unit at a time. Units may be further subdivided into one or more selectable status indicators comprising available radio, dispatched, en route, on scene, transporting, transport arrive, en route to post, on post, and out of service. Each of the one or more selectable status indicators may be displayed within the mapping application at a given time. In another embodiment, one of the one or more selectable status indicators may be displayed within the mapping application at a given time. Each of the one or more selectable status indicators may be assigned a color that may be displayed within the mapping application. The emergency unit displayed may be selectable within the mapping application, and a pop-up window may appear within the mapping application when the emergency unit is selected. The pop-up window may provide one or more items comprising the unit number, names of the crew members, the amount of time remaining in the unit's shift, current destination, velocity, call nature, scene location, and direction options. The system may track the status of the emergency unit as it approaches the end of its assigned shift and may display a number indicating the amount of time left in the assigned shift within the mapping application. Posts may be further subdivided into one or more categories that may be selectively displayable within the mapping application, the one or more categories comprising all posts, active posts, and post recommendations. A colored circle may be displayed within the mapping application around a response location, the colored circle gradually constricting as the time to respond decreases and wherein the color of the colored circle may correspond to the emergency unit assigned to respond to the call and the response location displayed within the mapping application. The system also may include a reporting module to evaluate the performance of the emergency unit responding to the call, wherein reports may be generated based on one or more parameters including date, type of call and timeliness of response to call.

Additional embodiments of the present disclosure may provide a system for replay evaluation of an emergency unit response to a call, the system comprising a module including a menu providing one or more selectable items and a mapping application, wherein the one or more selectable items may be selectively displayed within the mapping application as the emergency unit response to the call may be replayed within the system. More than one emergency unit response to a call may be displayed within the mapping application at a given point in time. Data associated with the one or more selectable items may be obtained from a live module that may evaluate an emergency unit response to a call in real-time.

BRIEF DESCRIPTION OF THE DRAWINGS

For a more complete understanding of this disclosure, reference is now made to the following description, taken in conjunction with the accompanying drawings, in which:

FIG. 3 depicts a view of a window that may be displayed within a mapping application when a unit has been selected according to an embodiment of the present disclosure;

DETAILED DESCRIPTION

Figure 1:
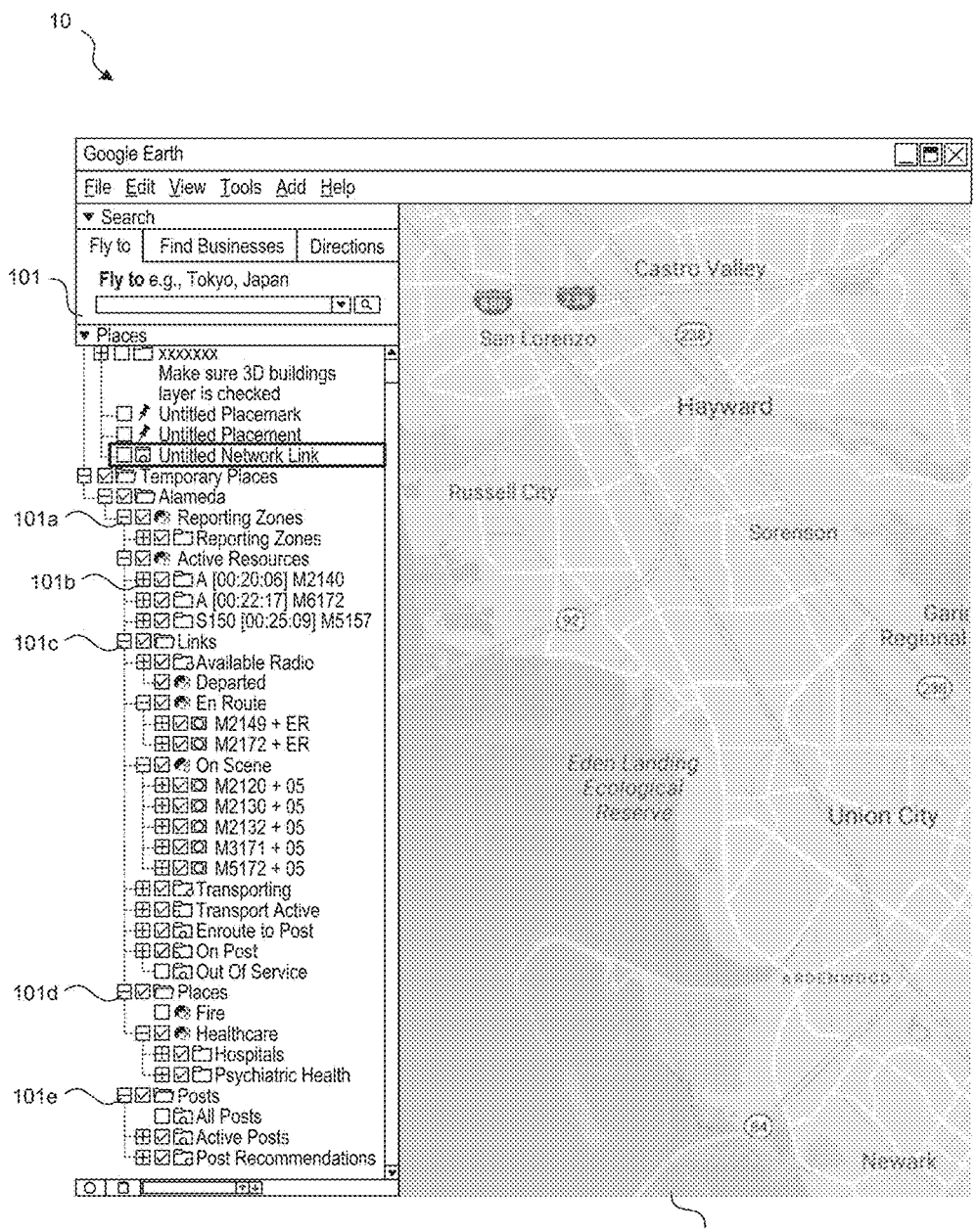
FIG. 1 depicts a view of a tracking module in operation according to an embodiment of the present disclosure.

Systems and methods for live utilization and tracking of vehicular movement may produce a fluid representation of the movement of vehicles and means to evaluate vehicle movement/activities relative to response requirements according to embodiments of the present disclosure. Accordingly, real-time evaluations and/or corrections may be made based on this improved tracking of movement/activities. Replay analysis of movement/activities that have already occurred may be provided in some embodiments of the present disclosure to evaluate and make adjustments for future responses and activities. Reporting also may be provided to summarize the results from utilization and tracking using systems and methods according to embodiments of the present disclosure.

Embodiments of the present disclosure may provide real-time tracking of emergency vehicles within a specified geographic location through a web-based mapping application, such as the Google Earth platform. Embodiments of the present disclosure also may provide for the display of items including but not limited to post locations, call locations, the allowable (contractual or otherwise determined) response time remaining to address individual emergencies, reporting zones, current unit status, posting recommendations as well as satellite imagery associated with the locations and reporting. Individual units may be analyzed; however, more than one unit also may be analyzed at any given time, thereby providing the ability to review and address actions of units both collectively and individually. By providing such real-time and/or historical dispatch and response information through systems and methods according to embodiments of the present disclosure, response time compliance may be addressed and emergency care may be improved without as much need for individual inquiries of units or dispatchers. Systems and methods according to embodiments of the present disclosure may be used to decrease response time thereby increasing responsiveness of the dispatchers and/or responding units.

Systems according to embodiments of the present disclosure may be divided into one or more modules to address various dispatching, tracking, review and reporting needs. These modules may be referred to as "Pulse Live," "Pulse Replay" and "Pulse Reporting." Each of these modules may provide information that may assist in determining the most appropriate unit to respond to a given call and/or evaluating whether the responding unit was the most appropriate unit to respond.

It should be appreciated that each module may run independently while data may be shared between the modules according to embodiments of the present disclosure. Accordingly, a system may include each of these modules, less than all of these modules, or additional modules without departing from the present disclosure. Systems incorporating one or more of these modules may be installed within vehicles to provide mapping intelligence as well as means to communicate with dispatchers, controllers and operation managers. It also should be appreciated that dispatches, controllers and operation managers similarly may utilize systems according to embodiments of the present disclosure to monitor and direct vehicle movement and response in real-time as well as to evaluate previous responses through replay and report of responses and vehicular movement. Each of the modules may be integrated with an existing web-based or online mapping application, such as Google Earth, or other similar mapping applications that may be later developed according to embodiments of the present disclosure.

A first module that may be utilized within systems according to embodiments of the present disclosure may be referred to as "Pulse Live." The "Pulse Live" module may provide a real-time mechanism to evaluate, monitor and track calls as they are processed and acted upon within systems according to embodiments of the present disclosure. A call may be received and processed by a dispatcher, for example, to assign the call to a unit for response. In embodiments of the present disclosure, the unit associated with a particular call may be assigned a color that corresponds to the call response location.

In some embodiments of the present disclosure, a line may be depicted within the mapping application to connect the unit to the response location. This line may be colored to correspond to the color that has been assigned to the unit and the response location to simplify the mechanism for a dispatcher to follow the unit as it travels to the response location. A unit also may utilize the line to track its progress as it travels a route to respond to a call. It should be appreciated that the line initially connecting the unit to the response location may not necessarily correspond to a street routing network (i.e., may not map the route) but rather may be depicted "as the crow flies" without departing from the present disclosure. As the route for the unit to travel to reach the response location is generated, the line connecting the unit to the response location may change/update to correspond to the route selected according to embodiments of the present disclosure. Similarly, a user may change the route based on traffic or other issues that may arise during travel to a response location, and the line may change accordingly.

FIG. 1 depicts a view of "Pulse Live" module 10 in operation according to an embodiment of the present disclosure. "Pulse Live" module 10 may include menu 101 as well as mapping application 102; however, additional features may be incorporated into module 10 without departing from the present disclosure. Menu 101 may include various selectable items that may be mapped within mapping application 102 including but not limited to reporting zones 101a, active responses 101b, units 101c, places 101d and posts 101e as will be discussed in more detail below. Selecting a box associated with any of these items depicted within menu 101 may cause the individual item to be depicted within mapping application 102. Similarly, unselecting any item within menu 101 may cause that particular item(s) to disappear from view within mapping application 102. While dropdown menus and check boxes have been utilized within menu 101 depicted in FIG. 1, it should be appreciated that other selection mechanisms may be utilized to identify items to be mapped within mapping application 102 without departing from the present disclosure.

Menu 101 may include reporting zones 101a that also may be referred to as emergency response zones according to embodiments of the present disclosure. For a given geographic location, such as a county, there may be one or more reporting zones. For example, reporting zones may constitute cities or other unincorporated areas within a county. However, it should be appreciated that there may be more or fewer reporting zones established for a given geographic location than are depicted in FIG. 1 without departing from the present disclosure. In this embodiment, all of reporting zones 101a have been selected for display within mapping application 102 as the box associated with reporting zones 101a has been checked within menu 101. However, there may be other embodiments wherein less than all of the reporting zones for a given geographic location may be selected, and in those embodiments, only the selected reporting zones would be viewable through mapping application 102.

Menu 101 also may include active responses 101b that may provide an indication of the real-time status of calls that may be in the process of being responded to (or require response) by one or more units. Various items of information may be included as part of active responses 101b including but not limited to the determinant, time remaining before the response would be considered late (which may be based on contractual obligations of the entity controlling units responding to a call), and an identification of the unit(s) assigned to respond to a call. Active responses 101b within menu 101 indicates that there are three active responses within the embodiment depicted in FIG. 1. Each of these active responses has been selected within menu 101 to have their respective positions and actions displayed within mapping application 102. It should be appreciated that more or fewer active responses may be selected for display within mapping application 102 at any given time. Accordingly, a user may elect to view less than all of the available active responses within menu 101 without departing from the present disclosure. Each response may be labeled according to its location determinant as well as the amount of time remaining before the response may be considered untimely or late.

Units 101c also may be selected within menu 101 to be displayed within mapping application 102 according to embodiments of the present disclosure. It should be appreciated that units 101c may refer to individual vehicles responding to a call and units 101c may be organized based on the status of different units so that it may be possible to elect to display all of the units that fall within a specified unit status at any given time according to embodiments of the present disclosure. Units 101c may provide the status of all active units, and it should be appreciated that units 101c within menu 101 may be expanded so that a user may selectively display different unit status within mapping application 102 at any given time. As depicted in menu 101 of FIG. 1, units 101c may be sorted based on various unit status indicators including but not limited to available radio (AR), dispatched (DP), en route (ER), on scene (OS), transporting (TR), transport arrive (TA), en route to post (EP), on post (OP), and out of service (OU) according to embodiments of the present disclosure. While each of these unit statuses are listed as part of units 101c, it should be appreciated that more or fewer unit status indicators may be utilized at any given time without departing from the present disclosure. It also should be appreciated that a user may elect to display all units regardless of status within mapping application 102 by selecting each of the unit statuses within units 101c. For example, in FIG. 1, all unit status indicators except for those units identified as being out of service are selected for display within mapping application 502. If a user elected to also view units that are out of service (i.e., a unit that may be on break but can be disturbed if a high priority call arises that is in an area where the unit may be of service), the user may select the box associated with those units as part of units 101c and those units may then be displayed though mapping application 102.

Figure 2:
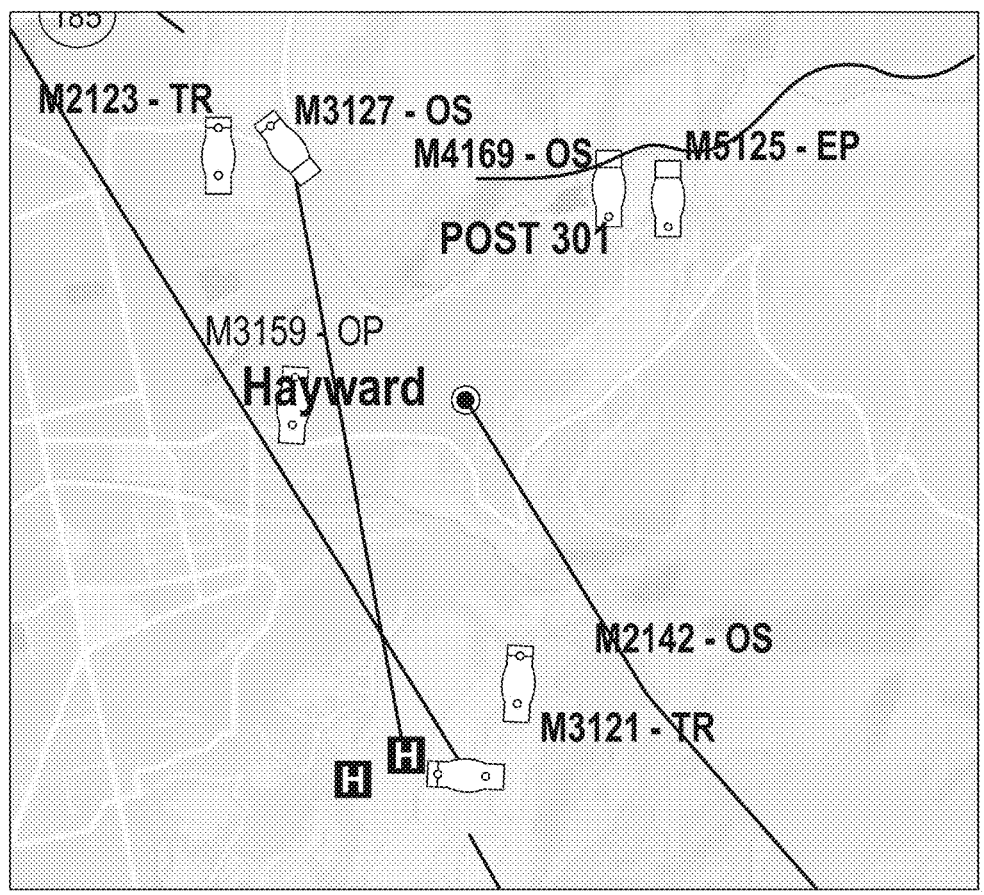
FIG. 2 depicts status and movement of several units mapped within a mapping application integrated with systems and methods according to an embodiment of the present disclosure.

FIG. 2 depicts the status and movement of several units mapped within a mapping application integrated with systems and methods according to an embodiment of the present disclosure. In this embodiment, M2123 may be designated with a "TR" reflecting that it is transporting, and it may have an assigned color that may indicate the type of call being responded to and/or the location to which the unit is transporting (i.e., a particular hospital). M3121 also is designated as "TR" to reflect that it is transporting but it may have a different assigned color than M2123 to reflect that it is responding to a different call and/or transporting to a different location. M3127 may be designated with an "OS" to reflect that is on the scene of a specified call and may be designated with a particular color to reflect the type of call and/or its location. Similarly, M2142 may be on the scene of a particular call and may be designated with a different color to reflect the type of call and/or its location. M3159 may be designated as "OP" to reflect that is on post while M5125 may be designated as "EP" as it is en route to post. Post 301 may be displayed within the mapping application to reflect that it is currently recommended to be filled but is not yet filled by a unit.

Similarly, a user may elect to display units within a specified status identifier by expanding the dropdown menu associated with that status identifier. For example, in FIG. 1, five units have been designed with the status identifier of "on scene," and the user has elected to view each of these five units within the mapping application. However, if the user wished to focus on a single unit, such as M2120, the other units within that status identifier may be unselected and then later reselected (if the user decides that he/she wants to display them again).

In embodiments of the present disclosure, selecting the unit displayed on a mapping application, such as mapping application 102, may provide more detailed information about that particular unit. FIG. 3 depicts a view of window 40 that may be displayed as a pop-up within the mapping application when a unit has been selected. Window 30 may provide information associated with the selected unit including but not limited to the unit number, names of the crew members, the amount of time remaining in the unit's shift, current destination, velocity, call nature, scene location and/or direction options. Direction options may include hyperlinks such that selecting one of the hyperlinks may provide directions to or from the unit's current destination (or to or from a post or other location). However, other mechanisms for providing directions may be included in window 30 without departing from the present disclosure. Scene or destination locations as well as post locations also may be selectable icons within the mapping application wherein a window may provided to obtain directions or other route information.

Systems formed according to embodiments of the present disclosure also may track the status of units as they approach the end of their respective shifts. For example, once a unit enters the last hour of its assigned shift, the number "60" may appear in parentheses to the right of the unit's current status within the mapping application. This number may be associated with a timer that may count down in real time until the unit's last hour has been eclipsed. Should the unit still be on duty at the end of that hour or at the end of the countdown, the timer may display a negative number in parentheses indicating the number of minutes that the unit has been held over past the end of its shift. It should be appreciated that the number that appears may change depending on contractual requirements or the specific length of a given unit's shift without departing from the present disclosure. It also should be appreciated that this "end of shift" indicator may not place any restriction on whether the unit can be assigned an emergency call or a post move.

Places 101d also may be selected for display within mapping application 102 according to embodiments of the present disclosure. Places 101d may include particular facilities or other points of interest, including but not limited to fire stations, hospitals and psychiatric facilities within a given geographic location. However, it should be appreciated that other facilities or points of interests may be included as part of places 101d without departing from the present disclosure. A user may selectively display one or more of the facilities or points of interest categories within places 101d by selecting each category within menu 101. In the embodiment depicted in FIG. 1, the user has elected to only view places 101d associated with healthcare (i.e., hospitals and psychiatric health facilities) and accordingly has left fire departments unchecked. This may occur in a situation where the unit is an ambulance that may be dispatched to the scene to assist someone with a medical emergency, and the unit and/or dispatcher would need to be able to identify the closest healthcare facilities that may be available to transport the patient. As fire stations would not be the likely places to provide medical services, the unit would not have a need to view where fire stations are located within mapping application 102. However, if a dispatcher is tracking movement of both fire trucks and ambulances, for example, the dispatcher may elect to display both fire stations and healthcare facilities within mapping application 102 in order to direct the units from and to a response location in a timely manner. It also should be appreciated that the categories within places 101d may be further subdivided so that a user may elect to view individual hospitals or psychiatric health facilities listed within the category. This may be helpful, for example, if the dispatcher or the unit being dispatched needs to view particular facilities where the patient's physician is credentialed to practice and could treat the patient upon arrival.

Posts 101e may be selected for display within mapping application 102 according to embodiments of the present disclosure. It should be appreciated that posts 101e may be brick and mortar posts or side-of-the-road posts within a given geographic location. The number and location of posts may vary depending on the requirements within a response zone and/or as set forth in contractual obligations for providing emergency or other services in a given geographical location or within one or more response zones. Contractual obligations may identify the maximum distance between posts within a response zone needed to keep the response time needed to respond to any call at a minimum. For example, posts may be locations where ambulance units are required to be positioned so that they may be easily dispatched to different reporting zones, particularly if some areas within a given reporting zone may not be located within a reasonable distance from a hospital or other emergency response location where an ambulance unit might typically be stationed. In an embodiment of the present disclosure, active posts where units are positioned at any given may be displayed as green Xs with the name (full or abbreviated) of the post written in green text. However, another color may be used to designate an active post without departing from the present disclosure.

Menu 101 may permit a user to selectively display posts 101e within mapping application 102. For example, a user may elect to display all posts within a given geographical location on mapping application 102. In other instances, a user may elect to only display active posts or just post recommendations within mapping application 102. FIG. 1 depicts a view wherein the user has elected to view active posts and post recommendations within mapping application 102. It also should be appreciated that within the categories in posts 101e, a user may utilize dropdown menus or other selection mechanisms associated with the categories to view specific posts within each category. For example, a user may elect to just view certain active posts or only post recommendations without departing from the present disclosure. If only active posts are to be displayed, the system may display the posts currently needing to be filled based on a system status plan according to embodiments of the present disclosure. If post recommendations are to be displayed, lines traced from a recommended unit to a recommended post may indicate recommended post moves.

Figure 4:
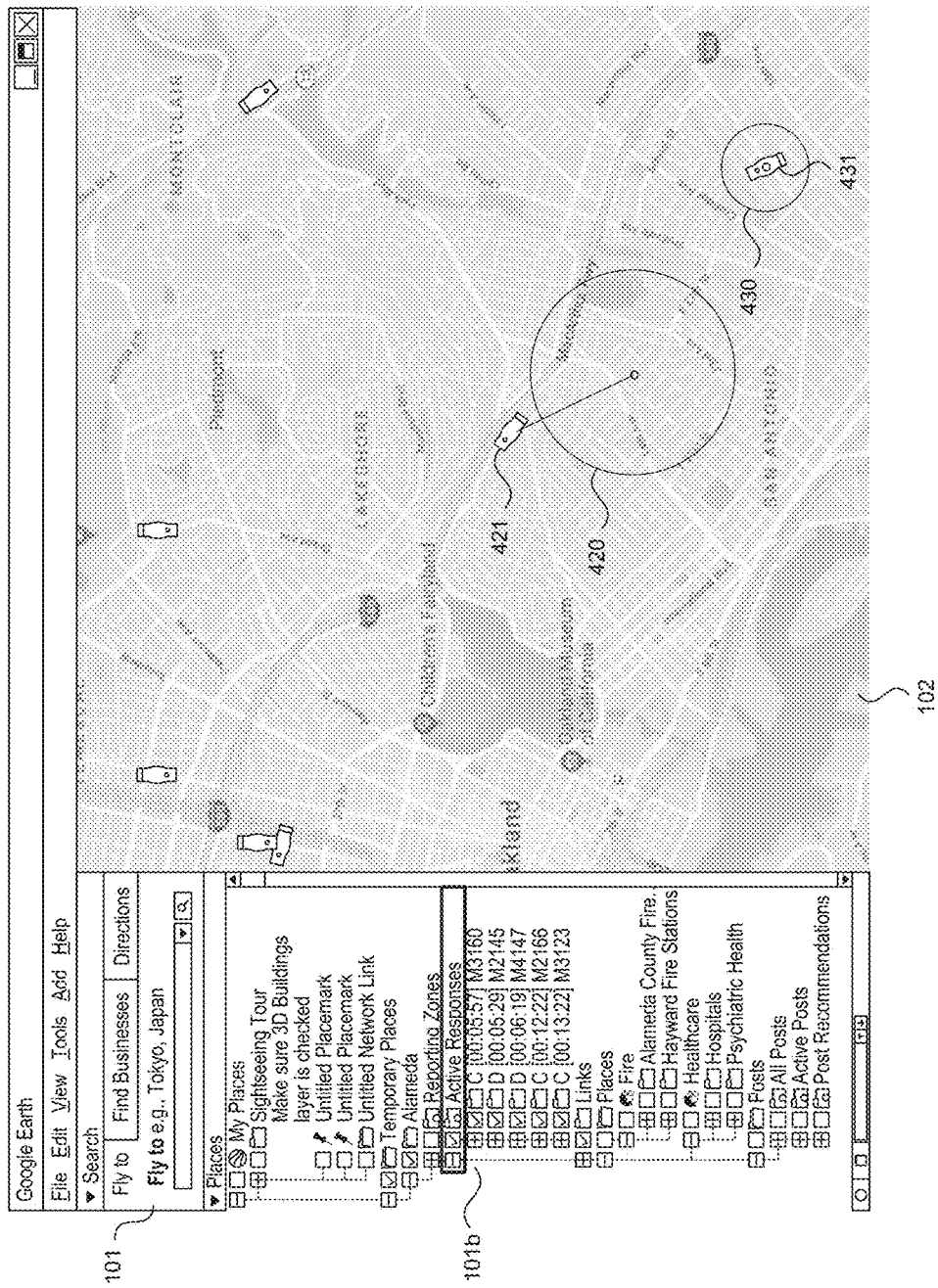
FIG. 4 depicts another view of a mapping application with menu according to an embodiment of the present disclosure.

FIG. 4 depicts another view of mapping application 102 with menu 101 according to an embodiment of the present disclosure. In this view, the user has elected to display only active responses 101b within mapping application 102. For each active response, it should be appreciated that a specified amount of time that the unit associated with the active response may be set for the unit to arrive at the scene (or respond to the call). Colored circles 420, 430 may be displayed within mapping application 102 to surround the scene location and to provide a real-time view of the remaining time left before the respective units 421, 431 associated with certain active responses would be considered "late" to respond. What is defined as "late" may be set through contractual obligations or otherwise established according to embodiments of the present disclosure. Colored circles 420, 430 may gradually constrict as the requisite response time diminishes. Once the circle has disappeared from view on mapping application 102, this may provide the user with an indication that the response was late. It should be appreciated that there is no limitation as to the number of colored circles that may be displayed within mapping application 102. Further, while circles have been used as the graphical representation of time left to respond to call in this embodiment, it should be appreciated that other shapes or indicators may be utilized to show remaining response time without departing from the present disclosure.

Figure 5:
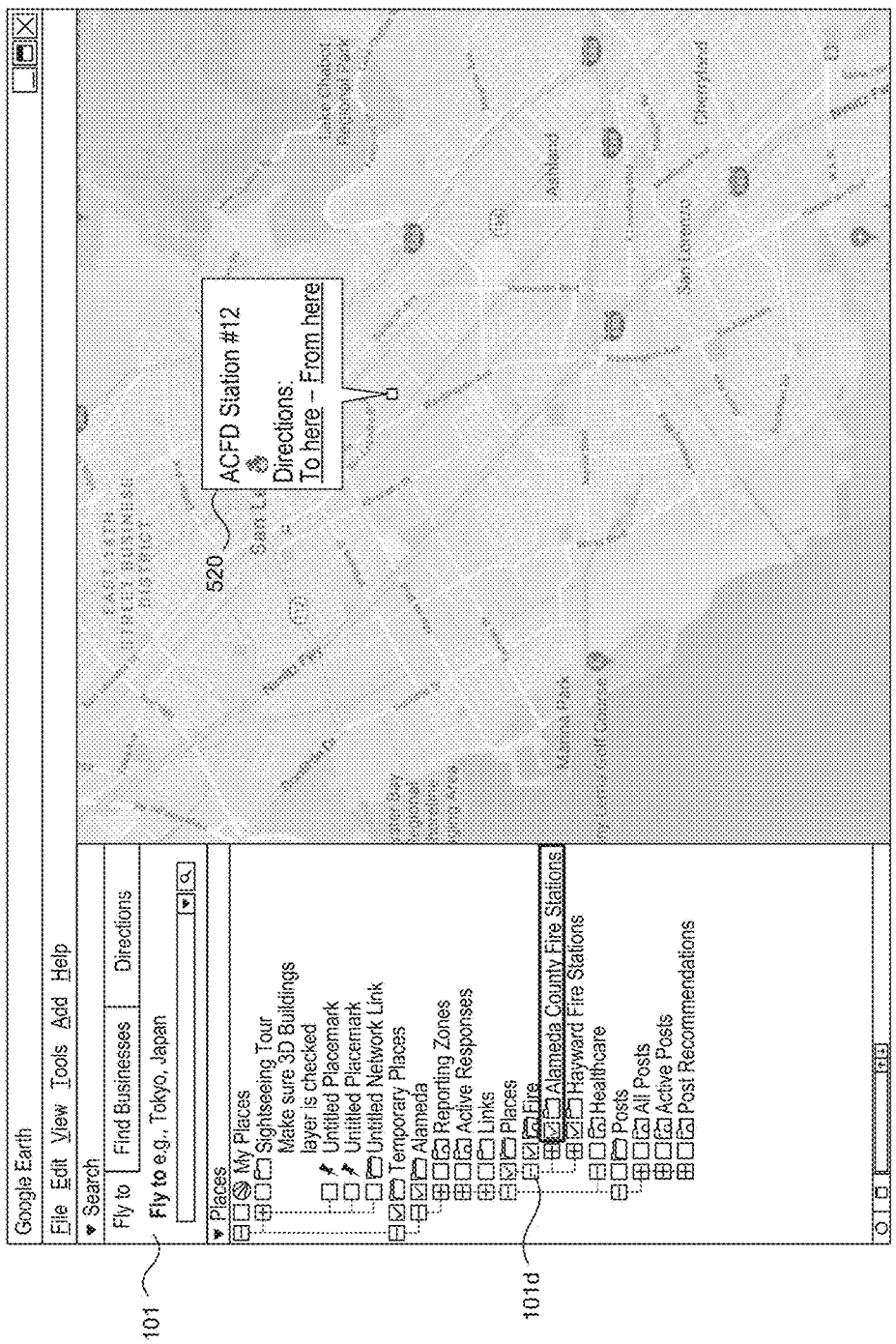
FIG. 5 depicts another view of a mapping application with menu according to an embodiment of the present disclosure.

FIG. 5 depicts another view of mapping application 102 with menu 101 according to an embodiment of the present disclosure. In this view, the user has elected to display only the fire stations within a specified geographic area as part of places 101d. This view may be of assistance to a dispatcher who may wish to identify the fire stations within a response zone and determine which one may be closest to a scene associated with a call. It also may be of assistance when the dispatcher has identified the fire station from which to dispatch a fire truck unit to a scene, and he/she may need to provide directions to the scene from the fire station. In other embodiments, a fire truck may have been dispatched to respond to a call, completed its response and then requires directions to return to the fire station. In this embodiment, the user may identify the fire station within mapping application 102 and then select the fire station (such as by double clicking the fire station). Once the fire station has been selected, pop-up window 520 may appear within mapping application 102 providing the user with one or more hyperlinks to obtain directions to the fire station or from the fire station to another location. The hyperlinks may be associated, for example, with the Google Maps API that may provide the mapping or other directional information for mapping application 102. However, other mapping APIs or tools may be utilized without departing from the present disclosure.

Figure 6:
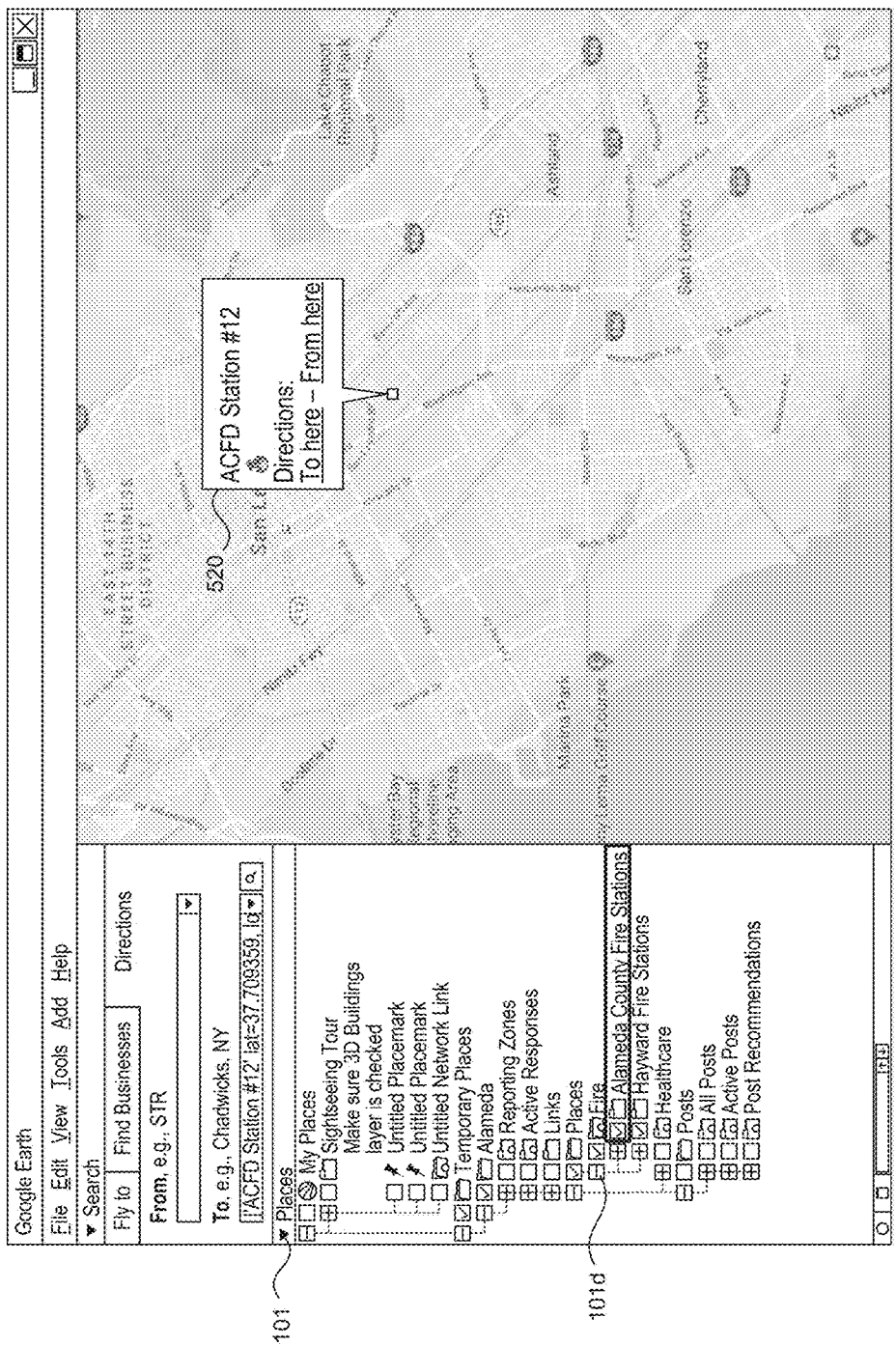
FIG. 6 depicts another view of a mapping application with menu according to an embodiment of the present disclosure.

FIG. 6 depicts another view of mapping application 102 with menu 101 according to another embodiment of the present disclosure. In this embodiment, the user has utilized pop-up window 520 depicted in FIG. 5 to identify directions to the fire station. Once the hyperlink associated with "to here" has been selected within window 520, the latitude/longitude information associated with the given fire station may be populated within mapping application 102 to create a route from a starting location (i.e., the scene of an incident) to the fire station. It should be appreciated that once a route is depicted within mapping application 102, the user may alter the route through selecting and moving the route, such as by use of a mouse or track pad or other selection mechanism, according to embodiments of the present disclosure.

Accordingly, embodiments of the present disclosure may provide information about the time that a unit has left to reach the scene based upon contractual obligations or the needs of the patient or others associated with an incident (i.e., homeowner or business owner). The dispatcher may also be provided with information to determine the best unit to respond to a particular call, such as based on proximity of the unit to the scene associated with the call. It should be appreciated that a dispatcher may use systems and methods according to embodiments of the present disclosure to assign, unassign and/or reassign units to calls. For example, if a higher priority call is received, a unit may be traveling to respond to one call but then may be reassigned to that higher priority call because of its proximity to the scene of the higher priority call. Accordingly, the first call may be assigned to another unit for response. This may provide for real-time shifting of units to respond to different calls, thereby improving the timeliness of the response. This may be particularly helpful insofar as a dispatcher may be asked to address both emergency and non-emergency calls, wherein some calls may have higher priority than other calls.

A second module that may be utilized within systems according to embodiments of the present disclosure may be referred to as "Pulse Reporting." This module may provide various tools for a user to evaluate performance of units responding to calls and/or dispatchers sending out units to respond to calls according to embodiments of the present disclosure. Reports provided through this module may be compiled and organized based on one or more parameters including but not limited to date ranges, types of calls, and/or calls where the responding unit was late to respond to the call. The reporting provided through this module may include reporting that may be required to show compliance with contractual obligations. When a report is created through this module, the report may include hyperlinks associated with each call or item included within the report so that a user may access the hyperlinks in order to obtain additional information about one or more calls. Additional information may include but is not limited to type of call, event comments, and unit status changes during the call. It should be appreciated that reporting through this module may provided in various formats, including but not limited to Excel, Word, Access or other web-based outputs.

A third module within systems according to embodiments of the present disclosure may be referred to as "Pulse Replay." The "Pulse Replay" module may provide a user with the ability to select a call that has already occurred, replay the call in real-time as it would have been depicted in the "Pulse Live" module and compare that call to other activity that was going on in a geographical location or within a response zone during the same time frame. For example, a user may wish to review and analyze a call where the responding unit was late in order to determine whether the unit was late due to the timeliness of receiving the call from the dispatcher or because of some other issue, such as the unit taking a less than optimal route to respond to the call or the most appropriate unit was assigned to respond to the call. When a call is reviewed through the "Pulse Replay" module, the user may identify information including but not limited to, when the unit received notice of the call, where the unit was located when the call was received, the route that the unit took to arrive at the scene, whether the route was the most direct route, and/or whether the unit encountered delays in arriving at the scene. For example, in order to evaluate if the most appropriate unit was assigned to respond to the call, the "Pulse Replay" module may permit a user to review snapshots of units that were located within a response zone at the time when the call was received by the dispatcher. A user also may review the accuracy of the end point (scene of the call) identified through the mapping application, such as to determine if other mapping or directional applications should be used to provide more accurate directions to respond to a call. A user also may utilize the "Pulse Replay" module to evaluate how quickly units are typically moving to respond to a call once they are assigned. Accordingly, this module may be helpful for use in training, defending against claims, analyzing, and/or posting (i.e., determining where best to position units relative to response zones). The "Pulse Replay" module may utilize a menu and/or mapping application in a manner similar to that depicted, for example, in FIGS. 1-6, but to review historical data rather than real-time data.

It should be appreciated that calls may be evaluated through this "Pulse Replay" module on a daily basis or less or more frequently according to the needs or requirements of the user. In embodiments of the present disclosure, calls to be replayed through this module may be saved in a manner that may clip or excise out non-essential information related to the call in order to make playback within the module more efficient. It should be appreciated that calls may be stored for use within the "Pulse Replay" module for a specified period of time. In an embodiment of the present disclosure, the calls may be stored for 13 months. However, calls may be stored for longer or shorter periods of time without departing from the present disclosure.

It also should be appreciated that playback within the "Pulse Replay" module may be expanded to review activity occurring within a response zone or related to one or more specified units for a period of time prior to receipt or assignment of the call and/or for a specified period of time following the response to the call. The "Pulse Replay" module may work in conjunction with the "Pulse Live" module so that information stored and captured during use of the "Pulse Live" module may be used by the "Pulse Replay" module in order to function to review a particular call or response.

As discussed above, a mapping application utilized within systems and methods according to embodiments of the present disclosure may be color coded in order to maximize the amount of information that may be relayed visually to a user. Colors and other unique display items may be used to highlight different activities, movements and/or timing for completion within the online mapping application utilized in conjunction with embodiments of the present disclosure. For example, reporting zones may be outlined and shaded. Units available to respond to calls may be displayed with information including but not limited to their unit number and an abbreviated status indicator. It also should be appreciated that different colors may be utilized to delineate among available, assigned and out-of-service units, supervisor units, units nearing the end of their respective shifts. Further, scene locations may be color-coded based on, for example, the priority level or type of the call associated with the location according to embodiments of the present disclosure. A user also may utilize color-coding that may indicate whether an item being displayed is "live" or otherwise active. For example, if a green orb appears within the mapping application, the particular item may be designated as "live." If an update is being made to a particular item, the orb associated with the item may temporarily turn yellow during the update and then return to green when the update has been completed. If the orb turns red and remains red for any specified length of time, this may indicate that the item has stopped updating and/or there may be a problem with the system that needs to be addressed. While certain colors have been specified to indicate activity associated with a given item, it should be appreciated that other colors may be substituted without departing from the present disclosure.

Different line designations also may be used within a mapping application according to embodiments of the present disclosure. A solid line may be used to denote a unit's present specified route to respond to call, and the line may color-coded to correspond to that unit's status. It also should be appreciated that different colored lines may be depicted within the mapping application to indicate different activities. For example, white lines may be used to correspond to units assigned to post moves while black lines may be used for units transporting a patient. Colored lines may be used for units en route to an active incident wherein the color of the line may correspond to the type or priority level of the call. Using this information, a user may quickly identify the unit involved, what level of call the unit is responding to, and where the unit is located and where the unit may be traveling.

Layering of different mapping displays also may be provided such that a user may toggle between various map layers that may be displayed within a mapping application according to embodiments of the present disclosure. For example, a roads layer may be selected so that a user may view the road layout within a given geographic location along with block ranges and/or exit numbers according embodiments of the present disclosure. Embodiments of the present disclosure may, for example, utilize the Google Earth street view tool so that road segments may be viewable on the map. This may be helpful with difficult-to-locate calls or calls in which the caller can only provide directions and landmarks but perhaps may not have a street address available to provide. A weather layer may be applied to display the weather conditions within a given geographic location and/or an overlay of the current Doppler radar images. A places layer may display the names of businesses, government offices, parks and/or other places that may be recognized through the mapping application. A traffic layer may provide a display of the current traffic conditions of major thoroughfares within a given geographic location. A user also may elect to view different geographical borders (i.e., city, county or state) or labels (i.e., names of cities or communities) within a mapping application. It should be appreciated that the mapping application may allow for additional map layers that may provide a more in-depth view of a given geographical location, and these map layers may be utilized at the preference of the user according to embodiments of the present disclosure.

Systems and methods according to embodiments of the present disclosure may provide for storage and viewing of custom map layers, such as for use by the "Pulse Live" and "Pulse Replay" modules. For example, a folder may be created within the mapping application associated with a given geographic location wherein a user may select or deselect various items/layers to be displayed within the mapping application at any given time.

Systems according to embodiments of the present disclosure also may incorporate viewfinder tools. For example, tools may be provided so that a user may reorient the viewing window of the mapping application, such as to change the vantage point or move the viewing area of the geographic location be displayed. If a user withes to receive more specific labeling or a more detailed view of items within the mapping application, the user may utilize a zooming function according to embodiments of the present disclosure. Similarly, if a unit or other icon is depicted within the mapping application, the icon may be selected (such as by double-clicking), and the mapping application may permit the user to zoom in to focus on that particular icon according to embodiments of the present disclosure. It also should be appreciated that items depicted within a menu associated with a mapping application may be configured to be expandable, such as through dropdown menus, so that a user may select or deselect items associated with a layer for viewing within the mapping application.

It should be appreciated that response units utilizing systems and methods according to embodiments of the present disclosure may each include on board gateways with GPS receivers and/or PC mobile data terminals in order to view and manipulate the mapping application within the units while on duty. Information concerning the status and/or activities of the response unit may be transmitted through cellular, audio, video and/or other wireless communication mechanisms. The modules operating within systems and methods according to embodiments of the present disclosure may operate via the Internet or otherwise be online or web-based, utilizing a server and database structure, and accordingly may be more stable, have more flexibility in where and how they may be used, and lessen the resources needed to operate the systems and methods according to embodiments of the present disclosure.

While only three modules have been described as incorporated within systems according to embodiments of the present disclosure, it should be appreciated that other modules may be included within or utilized by these systems and methods without departing from the present disclosure. It also should be appreciated that systems may be formed that do not include all three modules that have been described insofar as the modules may operate independently from each other. However, if more than one of the modules is incorporated into a system, it should be appreciated that data may be shared among the modules according to embodiments of the present disclosure.

While systems and methods have been described with respect to emergency vehicles such as ambulances and fire trucks, it should be appreciated that systems and methods according to embodiments of the present disclosure also may be applicable to other means for transport that may or may not be emergency in nature but still may require tracking or monitoring.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

The invention claimed is:

1. A hosted server system for improved tracking of vehicular movement associated with one or more emergency units based on interactions between a database and at least one mapping application, the system comprising
    one or more databases coupled to the hosted server and storing instructions configured to:
        evaluate the vehicular movement associated with the one or more emergency units;
        receive at least one incoming call associated with at least one incident;
        prioritize, at the hosted server system, the at least one incident with respect to other incidents, wherein the at least one incident is identified as a prioritized incident;
        assess one or more attributes of paths connecting locations of the one or more emergency units to a response location corresponding to the prioritized incident;
        assign an emergency unit of the one or more emergency units to the response location associated with the prioritized incident;
        provide, by the hosted server, information for a time-varying display of an associated path of the emergency unit on a map via the at least one mapping application communicably coupled to the hosted server, which path indicates perceptible feedback that changes with time based on progress of the emergency unit to the response location;
        store, in the one or more databases coupled to the hosted server system, data concerning the vehicular movement; and
        track the vehicular movement associated with the one or more emergency units for evaluating the data concerning the vehicular movement via the at least one mapping application.

2. The system of claim 1, further comprising instructions to:
    generate a report of an incident of interest based on the data concerning the vehicular movement and at least one call associated with the incident of interest, wherein the report includes at least one of: a date of the at least one call, a type of the at least one call, and a timeliness of response to the call.

3. The system of claim 1 wherein the instructions to track the vehicular movement include instructions to selectively display at least one of the following items within the at least one mapping application:
    a post location, a call location, an allowable response time remaining to reach a call location, a reporting zone, a current unit status, and satellite imagery associated with a post or call location.

4. The system of claim 1, wherein the one or more attributes of paths connecting the location of the one or more emergency units to the response location includes: weather surrounding the location of the one or more emergency units or the response location, traffic conditions associated with the paths, landmarks associated with the paths, road conditions associated with the paths, one or more reporting zones associated with the paths, information associated with active responses handled by the hosted server, and information associated with active posts where other one or more emergency units are stationed.

5. The system of claim 4, wherein the one or more attributes of the paths are based on information included in the at least one mapping application.

6. The system of claim 1 further comprising instructions to:
    update the paths connecting the locations of the one or more emergency units to the response location based on changes in the one or more attributes.

7. The system of claim 1, wherein the tracking includes live tracking of the vehicular movement associated with the one or more emergency units in real-time or near real-time.

8. The system of claim 1, wherein the tracking the vehicular movement includes replaying the vehicular movement associated with the one or more emergency units, based on the data stored in the one or more databases coupled to the hosted server system.

9. The system of claim 1, wherein the at least one incoming call is included in a plurality of calls, the system further comprising instructions to:
    prioritize, at the hosted server system, multiple incidents based on the plurality of calls; and
    assign emergency units to response locations associated with each incident of the multiple incidents.

10. A hosted server system for improved live tracking and evaluation of an emergency unit in a plurality of emergency units qualified to respond to a call based on interactions between a database and at least one mapping application, the system comprising:
    one or more databases coupled to the hosted server, wherein the one or more databases are electronically coupled to:
        a module including one or more selectable items and the at least one mapping application communicably coupled to the hosted server, wherein the one or more selectable items is/are selectively displayed within the at least one mapping application as an emergency unit of the plurality of emergency units responds to the call; and
        a communication link to receive and transmit information related to the emergency unit responding to the call, wherein the one or more databases are configured for storing one or more attributes of a path connecting a location of the emergency unit to a response location associated with the call, and wherein the hosted server provides information for a time-varying display of an associated path of the emergency unit on a map via the at least one mapping application, which path provides perceptible feedback that changes with time based on progress of the emergency unit to the response location.

11. The system of claim 10, wherein the one or more selectable items comprise:

places, posts, and weather surrounding the location of the emergency unit or the response location, traffic conditions associated with the path, landmarks associated with the path, road conditions associated with the path, a reporting zone associated with the path, information associated with active responses handled by the hosted server system, and information associated with active posts where other emergency units are stationed.

12. The system of claim 11, wherein the active responses provide information about the determinant, time remaining before a response is considered late, and an identification of the emergency unit assigned to respond to the call.

13. The system of claim 11 wherein the plurality of emergency units are categorized according to one or more selectable status indicators comprising:

available radio, dispatched, en route, on scene, transporting, transport arrive, en route to post, on post, or out of service.

14. The system of claim 13, wherein the one or more selectable status indicators are displayed within the at least one mapping application at a given time.

15. The system of claim 13, wherein each of the one or more selectable status indicators is assigned a color that is displayed within the at least one mapping application.

16. The system of claim 10, wherein the path includes visibly perceptible feedback connecting the location of the emergency unit to the response location.

17. The system of claim 16, wherein the visibly perceptible feedback includes a line connecting the location of the emergency unit to the response location, wherein a color of the line corresponds to a status of the emergency unit assigned to the response location.

18. The system of claim 16, wherein the visibly perceptible feedback includes a line connecting the location of the emergency unit to the response location, wherein a color of the line corresponds to a priority level of the call.

19. The system of claim 10, wherein the at least one mapping application provides one or more items of information associated with the emergency unit comprising: the emergency unit number, names of the crew members, the amount of time remaining in a unit's shift, current destination, velocity, call nature, scene location, and direction options.

20. The system of claim 10, wherein the system is configured to track the status of the emergency unit as the emergency unit approaches an end of an assigned shift and display a number indicating an amount of time left in the assigned shift within the mapping application.

21. The system of claim 10, wherein the module is a first module, the system further comprising:

a second module to generate a report based on evaluation of performance of the emergency unit responding to the call, wherein the report includes at least one of: a date of the call, a type of the call, and a timeliness of response to the call.

22. A hosted server system for improved tracking and replay evaluation of an emergency unit responding to a call associated with an incident based on interactions between a database and at least one mapping application, the system comprising:

one or more databases coupled to the hosted server, wherein the one or more databases store instructions configured to replay vehicular movement associated with the emergency unit assigned to a response location associated with the incident, and provide, by the hosted server, information for a time-varying display of an associated path of the emergency unit on a map via the at least one mapping application, which path indicates perceptible feedback that changes with time based on progress of the emergency unit to the response location, wherein the path is based on at least one attribute connecting the location of the multiple emergency units to the response location.

23. The system of claim 22, wherein the at least one attribute of the path connecting the location of the emergency unit to the response location is selected from: weather surrounding the location of the emergency unit or the response location, traffic conditions associated with the path, landmarks associated with the path, road conditions associated with the path, a reporting zone associated with the path, information associated with active responses handled by the hosted server, and information associated with active posts where other one or more emergency units are stationed.

24. A system for improved live tracking and evaluation of an emergency unit responding to a call based on interactions between a database and at least one mapping application, the system comprising:

a hosted server accessible online and one or more databases coupled to the hosted server, wherein the one or more databases are electronically coupled to:

a module including a menu providing one or more selectable items and a mapping application configured to prioritize the call, wherein the one or more selectable items are selectively displayed within the mapping application as the emergency unit responds to the call; and a communication link to receive and transmit information related to the emergency unit responding to the call;

wherein the hosted server provides information for a time-varying display of an associated path of the emergency unit on a map via the at least one mapping application, and wherein the path includes display of an indicator in real-time surrounding a response location, the indicator configured to gradually constrict as a time to respond decreases.

25. The system of claim 24, wherein the mapping application displays a colored line connecting the emergency unit to a response location on a geographic map, wherein the color of the colored line corresponds to the priority level of the call associated with the response location.

* * * * *